(12) United States Patent
Ferrazzi et al.

(10) Patent No.: US 11,517,198 B2
(45) Date of Patent: Dec. 6, 2022

(54) METHOD AND SYSTEM FOR DOUBLE CONTRAST PERFUSION IMAGING

(71) Applicants: Siemens Healthcare Limited, Camberley (GB); King's College London, London (GB)

(72) Inventors: Giulio Ferrazzi, London (GB); Amedeo Chiribiri, London (GB); Karl-Philipp Kunze, Camberley (GB); Sarah McElroy, London (GB); Radhouene Neji, Camberley (GB); Sebastien Roujol, London (GB)

(73) Assignees: Siemens Healthcare Limited, Camberley (GB); King's College London, London (GB)

( * ) Notice: Subject to any disclaimer, the term of this patent is extended or adjusted under 35 U.S.C. 154(b) by 0 days.

(21) Appl. No.: 17/159,616

(22) Filed: Jan. 27, 2021

(65) Prior Publication Data

US 2021/0228080 A1 Jul. 29, 2021

(30) Foreign Application Priority Data

Jan. 27, 2020 (GB) .................................. 2001118

(51) Int. Cl.
| | |
|---|---|
| *A61B 5/05* | (2021.01) |
| *A61B 5/00* | (2006.01) |
| *A61B 5/026* | (2006.01) |
| *A61B 5/0275* | (2006.01) |
| *G01R 33/567* | (2006.01) |

(52) U.S. Cl.
CPC .......... *A61B 5/0044* (2013.01); *A61B 5/0263* (2013.01); *A61B 5/0275* (2013.01); *G01R 33/567* (2013.01)

(58) Field of Classification Search
CPC ... A61B 5/0044; A61B 5/0263; A61B 5/0275; A61B 5/055; G01R 33/4835; G01R 33/5601; G01R 33/56366; G01R 33/567; G01R 33/5673
See application file for complete search history.

(56) References Cited

U.S. PATENT DOCUMENTS

2017/0119259 A1 5/2017 Giri et al.

FOREIGN PATENT DOCUMENTS

EP 0997743 A2 5/2000

OTHER PUBLICATIONS

Guo et al., "Three-dimensional free breathing whole heart cardiovascular magnetic resonance T1 mapping at 3 T", JOurnal of Cardiovascular Magnetic Resonance, pp. 1-15 (Year: 2018).*
GB Combined Search and Examination Report dated Jun. 12, 2020, Application No. GB2001118.5.
(Continued)

*Primary Examiner* — Christopher L Cook
(74) *Attorney, Agent, or Firm* — Banner & Witcoff Ltd.

(57) ABSTRACT

The present techniques relate to a techniques for performing cardiac perfusion imaging in order to detect perfusion defects in the myocardium. The present techniques relate to methods for performing cardiac perfusion imaging by performing at least two image acquisitions using different, customizable saturation delay times, which improves the ability to detect defects.

13 Claims, 5 Drawing Sheets

(56) References Cited

OTHER PUBLICATIONS

Staeb, Daniel et al. "Gradient-controlled local Larmor adjustment (GC-LOLA) for simultaneous multislice bSSFP imaging with improved banding behavior" in Magnetic Resonance in Medicine, vol. 81, pp. 129-139, 2019.

Lui, Jun, et al; "Dynamic Cardiac MRI Reconstruction with Weighted Redundant Haar wavelets," Proceedings of the International Society for Magnetic Resonance in Medicine, 20th Annual Meeting and Exhibition, Melbourne, Australia; vol. 20, p. 4249, XP055102780; 2012.

Staeb, Daniel et al. "CAIPIRINHA Accelerated SSFP Imaging" Magnetic Resonance in Medicine, vol. 65, pp. 157-164, 2011 // DOI:10.1002/mrm.22600.

Weigel M.; "Extended Phase Graphs: Dephasing, RF Pulses, and Echoes—Pure and Simple", Journal of Magnetic Resonance Imaging vol. 41; pp. 266-295; 2015.

Nazir, M.S. et al. "Simultaneous multi slice (SMS) balanced steady state free precession first-pass myocardial perfusion cardiovascular magnetic resonance with iterative reconstruction at 1.5 T" in Journal of Cardiovascular Magnetic Resonance, 20, 84 (2018).

Staeb D, Speier P, Reiter T , Klink T , Neubauer H ,Bley T A ,Wech T,Max Weng A, Kstler H. Restating MS-CAIPIRINHA as an In-plane Acceleration Problem: An Efficient Method for Integrating High Coverage Cardiac Perfusion MRI into Clinical Workflow. ISMRM 2015. Abstract #2686.

Larkman, David J. et al. "Use of Multicoil Arrays for Separation of Signal from Multiple Slices Simultaneously Excited" Journal of Magnetic Resonance Imaging; vol. 13; pp. 313-317; 2001.

Breuer, Felix A. et al. "Controlled Aliasing in Parallel Imaging Results in Higher Acceleration (CAIPIRINHA) for Multi Slice Imaging" Magnetic Resonance in Medicine, vol. 53, No. 3, pp. 684-691, 2005 // DOI: 10.1002/mrm.20401.

Breuer, Felix A. et al. "Dynamic Autocalibrated Parallel Imaging Using Temporal GRAPPA (TGRAPPA)" Magnetic Resonance in Medicine, vol. 53, pp. 981-985, 2005.

* cited by examiner

FIG. 1A Conventional protocol (SB)
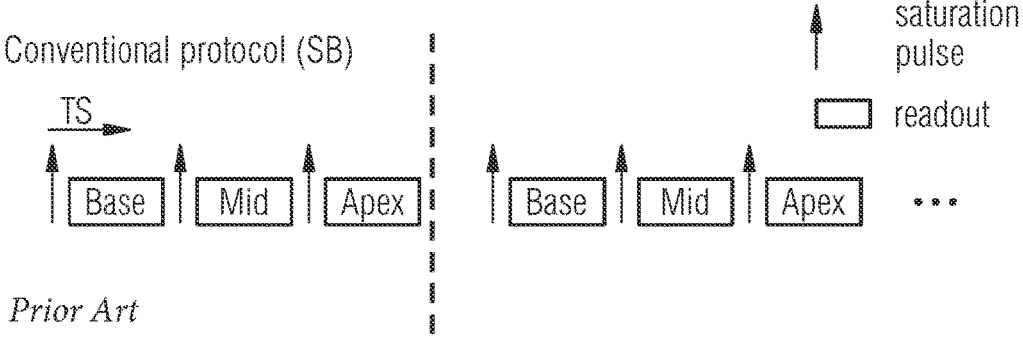
*Prior Art*
FIG. 1B Proposed (MB3)
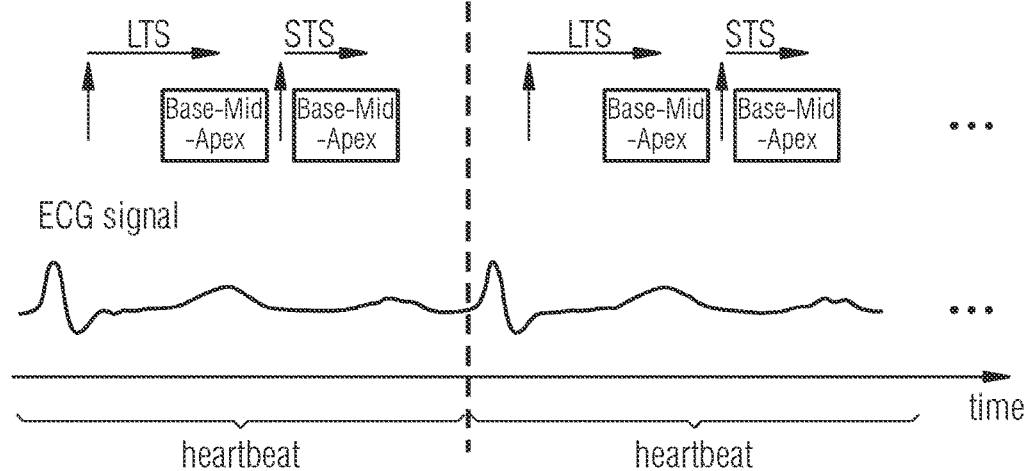

FIG. 3A
STS (130 ms)
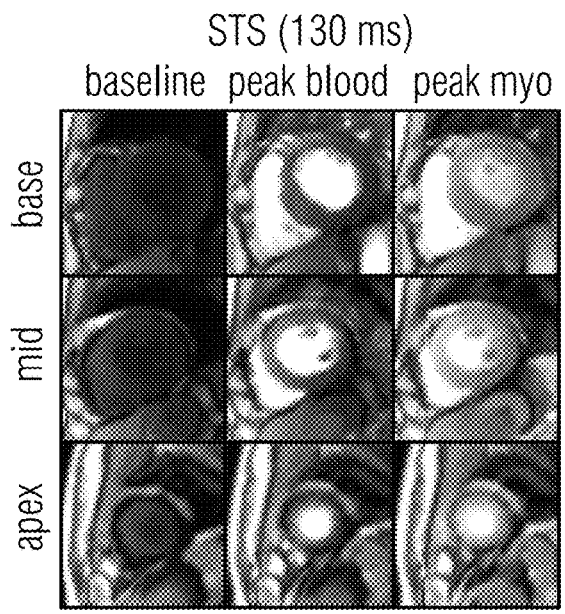
FIG. 3B
LTS (300 ms)
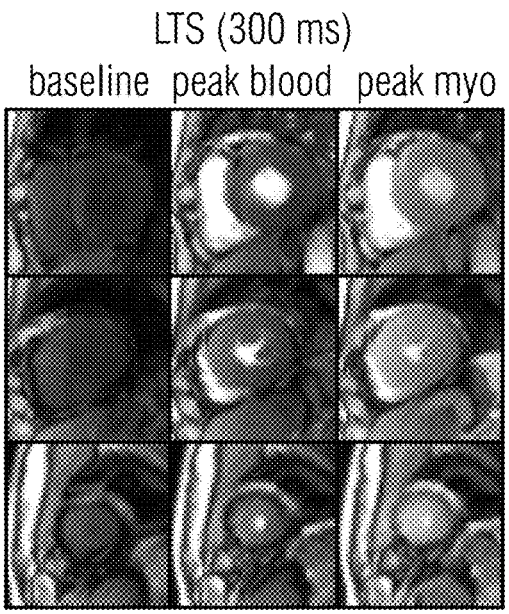
FIG. 4A
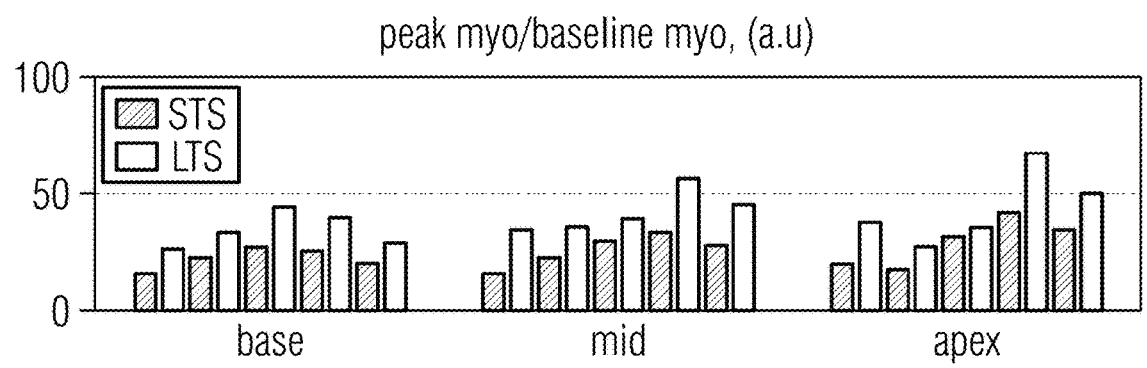
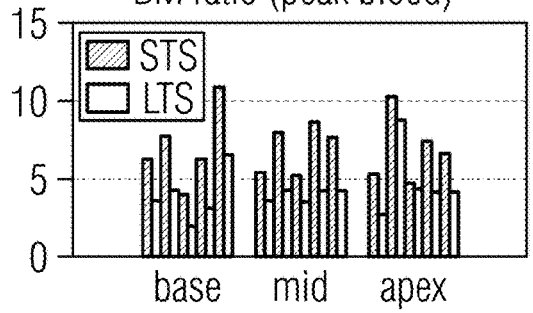
FIG. 4B
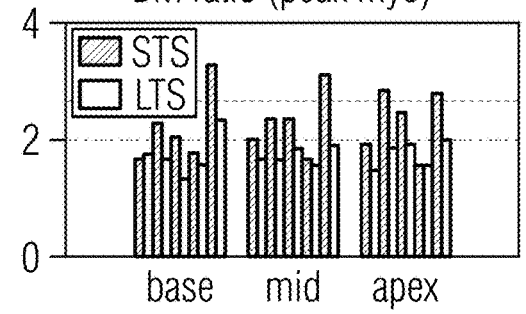
FIG. 4C

METHOD AND SYSTEM FOR DOUBLE CONTRAST PERFUSION IMAGING

CROSS-REFERENCE TO RELATED APPLICATIONS

The present application claims the benefit of the filing date of Great Britain patent application no. GB 2001118.5, filed on Jan. 27, 2020, the contents of which are incorporated herein by reference in their entirety.

TECHNICAL FIELD

The disclosure generally relates to a method and system for performing cardiac perfusion imaging in order to detect perfusion defects in the myocardium. In particular, the present disclosure relates to methods for performing cardiac perfusion imaging by performing at least two image acquisitions within each heartbeat using different, customizable saturation delay times, which improves the ability to detect defects whilst reducing signal ratio between blood and myocardium which reduces dark rim artefacts.

BACKGROUND

Cardiac magnetic resonance (CMR) perfusion imaging is widely used to detect perfusion defects in the myocardium. In a typical examination, a contrast injection is given that perfuses healthy and unhealthy or defective myocardial tissue in different ways, which in turn generates contrast in the final image. This contrast enables the defective tissue to be identified by a clinician. To boost contrast, a saturation pulse is employed to saturate the signal. The saturation pulse is separated from a magnetic resonance imaging (MRI) readout module that is used in the CMR perfusion imaging by a saturation delay time (TS), during which the magnetization recovers to baseline. Thus, TS is a key parameter that governs the contrast between healthy myocardium tissue and defective or unhealthy myocardium tissue. Furthermore, the length of TS determines a signal ratio between myocardium and blood (a factor influencing so-called 'dark rim artifacts'). However, longer than conventionally achieved TSs (~100 ms) would enable an increased contrast-to-noise ratio (CNR) between healthy and unhealthy myocardium, which is key for the diagnosis of coronary artery disease, and lower blood/myocardium signal ratios with subsequent reduced dark rim artifacts However, the clinical need to cover multiple slices (e.g. three or four) at base, mid, and apical regions within a single heartbeat constrains TS to be very short. Therefore, TS is suboptimal for the metric described above (myocardium to defect CNR, and myocardium to blood signal ratio). Furthermore, it is generally not possible to acquire the same slice location at different cardiac phases more than once.

Therefore, there is a desire to provide an improved method and system for capturing images to detect cardiac perfusion defects.

SUMMARY

To address these problems, the present techniques provide a method for cardiac perfusion imaging of a heart comprising: applying at least two saturation pulses during a cardiac cycle; performing at least two image acquisitions, each image acquisition taking place after one of the saturation pulses and after a different saturation time delay, and each image acquisition comprising simultaneously exciting at least two different slice locations in the heart and simultaneously obtaining at least two image slices.

The present techniques may be used with any suitable type of magnetic resonance imaging (MRI) readout module. For example, the MRI readout module may be any of balanced steady state free precession (bSSFP), gradient echo, echoplanar imaging, etc. It will be understood that these are non-limiting examples of MRI readout modules.

Conventional two-dimensional acquisition schemes sequentially acquire three or four slices within the same heartbeat by applying one saturation pulse for each slice and waiting the same short saturation delay time before performing the acquisition of another slice. The conventional two-dimensional acquisition schemes can provide high spatial resolution images, but are unable to acquire the same slice at different cardiac phases more than once. On the other hand, three-dimensional acquisition schemes enable data to be acquired faster, and may be used to perform multi-phase acquisition (i.e. imaging multiple phases of the cardiac cycle) using the same short saturation delay time. However, due to the time available to capture each cardiac phase, current three-dimensional acquistion schemes cannot be used to achieve high spatial resolution images in this context.

Thus, the present techniques remove the constraints imposed by conventional slice-by-slice two-dimensional acquisition schemes by using simultaneous multi-slice imaging techniques to acquire the same set of multiple slices during different cardiac phases within a single heartbeat, at different delay times. Each multi-slice acquisition in the different cardiac phases is performed after a customisable saturation time delay. This may advantageously reduce the overall number of acquisition modules that are needed. The resulting imaging protocol provides substantially the same spatial coverage as the current clinical standard (i.e. that provided by existing 2D slice-by-slice aquisition), but provides at least double temporal coverage and multi-contrast data.

It will be understood that the number of image acquisitions that may be performed within a cardiac cycle depends on the saturation time delays used for each image acquisition, the time required to perform each multi-slice acquisition, as well as the length of the cardiac cycle (which can vary from person to person, or under different conditions such as stress or relaxation). Thus, the present techniques perform at least two image acquisitions per cardiac cycle.

The step of applying at least two saturation pulses may comprise applying a first saturation pulse and a second saturation pulse, at different times during the cardiac cycle.

Thus, the step of performing at least two image acquisitions may comprise: waiting a first saturation time delay after application of the first saturation pulse; performing, after the first saturation time delay, a first image acquisition comprising simultaneously exciting at least two different slice locations in the heart and simultaneously obtaining at least two image slices; waiting a second saturation time delay after application of the second saturation pulse; and performing, after the second saturation time delay, a second image acquisition comprising simultaneously exciting the at least two different slice locations in a heart and simultaneously obtaining at least two image slices, wherein the second saturation time delay is of a different length to the first saturation time delay. That is, two (or more) sets or blocks of image acquisition may be performed (each obtaining multiple slices) in each cardiac cycle, each after a different time following a different saturation pulse. The first saturation time delay may be longer than the second saturation time delay, or vice-versa. The length of the first and second saturation time delays may be customized, e.g. selected to suit the patient or the cardiac phase.

The step of performing at least two image acquisitions may comprise using two-dimensional imaging, simultaneous multi-slice (SMS) imaging, or three-dimensional imaging. SMS imaging, also known as multiband (MB) imaging, employs complex radio-frequency pulses together with parallel imaging coil arrays to acquire several sections along the z-axis simultaneously. This enables a significant reduction in image acquisition time and the number of acquisition modules which are needed. Since SMS images can be obtained more quickly, it is possible to use different saturation time delays with each acquisition.

The step of performing the first image acquisition may comprise simultaneously obtaining at least two image slices during a first cardiac phase, and the step of performing the second image acquisition may comprise simultaneously obtaining at least two image slices during a second cardiac phase. The first cardiac phase may be during end systole, and the second cardiac phase may be during mid-diastole, but these are non-limiting examples of the cardiac phases during which image slices may be obtained. It will be understood that image acquisition may be performed during any two or more cardiac phases.

Generally, at least two image slices are obtained during each image acquisition. In a particular example, the steps of performing a first and second image acquisition may comprise simultaneously obtaining three image slices. The three image slices may correspond to basal, mid, and apical segments of the heart, but this is a non-limiting example of the different segments that may be imaged.

As mentioned above, saturation time delays that are longer than those used in conventional CMR perfusion imaging techniques may be used in the present techniques to improve the signal ratio and contrast-to-noise ratio. Typically, short saturation time delays of around 100 ms may be used in the conventional techniques. Thus, in the present techniques, one of the first saturation time delay and second saturation time delay may have a length in the range of 50 ms to 150 ms (i.e. a short time delay), and the other of the first saturation time delay and second saturation time delay may have a length in the range of 200 ms to 400 ms, or between 200 ms to 600 ms (i.e. a long time delay). It will be understood that both the first and second saturation time delays may be short or long time delays, of differing values. These ranges are non-limiting examples and the first and second saturation time delays may be any suitable values.

The present techniques also provide a (non-transitory) computer readable medium carrying processor control code that, when implemented in a system (e.g. executed by an image processor or other suitable processor) causes the system to carry out the methods described herein.

The present techniques also provide an image capture system for cardiac perfusion imaging of a heart. The system may comprise an image capture device that is configured to capture images using the method(s) described herein. The system may comprise a user interface which is configured to display the images captured by the image capture device.

BRIEF DESCRIPTION OF THE DRAWINGS/FIGURES

The above mentioned attributes and other features and advantages of this disclosure and the manner of attaining them will become more apparent and the disclosure itself will be better understood by reference to the following description of embodiments of the disclosure taken in conjunction with the accompanying drawings, wherein:

FIG. 1a shows a schematic diagram of an imaging sequence structure for a conventional perfusion imaging protocol;

FIG. 1b shows a schematic diagram of an example imaging sequence structure, in accordance with one or more embodiments of the present disclosure;

FIGS. 3a-3b show the outcome of in-vivo evaluation of an example imaging sequence structure, in accordance with one or more embodiments of the present disclosure;

FIGS. 4a-4c show a difference in contrast using short saturation time delays and long saturation time delays, in accordance with one or more embodiments of the present disclosure;

DETAILED DESCRIPTION

Figure 2A:
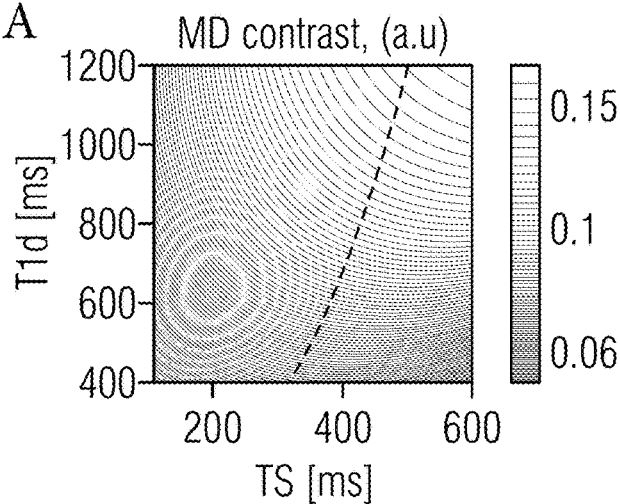
FIGS. 2a-2c show the outcome of numerical simulations used to study the relationship between saturation delay time, contrast between healthy and defective tissue, and signal ratio between blood and myocardium, in accordance with one or more embodiments of the present disclosure.

FIG. 1a shows a schematic diagram of an imaging sequence structure for a conventional perfusion imaging protocol. In the conventional acquisition scheme, multiple slices are acquired sequentially or one after another within a heartbeat by applying a saturation pulse, waiting a saturation delay time (TS), and obtaining a slice. In the imaging sequence structure shown in FIG. 1a, three slices are obtained one after another of the basal, mid, and apical segments of the heart. As shown, each slice is obtained at a different time point in a heartbeat, i.e. during a different cardiac phase. Furthermore, each saturation delay time is the same. As the slices are obtained sequentially, the saturation delay time has to be short to obtain images of the different slices within a heartbeat. Accordingly, the resultant images do not have a good signal ratio between myocardium and blood (a factor influencing so-called 'dark rim artifacts'), or a good contrast-to-noise ratio (CNR) between healthy and unhealthy myocardium, both of which are key for the diagnosis of coronary artery disease, and both of which depend on the length of TS. Specifically, the signal ratio between myocardium and blood in the resultant images is too high and the CNR is too low.

FIG. 1b shows a schematic diagram of an example imaging sequence structure, in accordance with one or more embodiments of the present disclosure. The new acquisition scheme comprises applying at least two saturation pulses during a cardiac cycle, and performing at least two image acquisitions, each image acquisition taking place after one of the saturation pulses and after a different saturation time delay. Each image acquisition comprises simultaneously exciting at least two different slice locations in the heart, and simultaneously obtaining at least two image slices. In FIG. 1b, two image acquisitions are performed sequentially (one after the other), but within each acquisition multiple slices are obtained simultaneously. The saturation time delay before performing each image acquisition is different and customizable.

In FIG. 1b, each image acquisition is shown as obtaining three slices of the basal, mid, and apical segments of the heart. It will be understood that this is a non-limiting illustrative example. More generally, two or more slices may be obtained during each image acquisition.

In FIG. 1b, the imaging sequence structure comprises applying two saturation pulses, each before an image acquisition block, but it will be understood that this is a non-limiting illustrative example, and more than two saturation pulses and more than two image acquisition blocks may be used in some cases. In this illustrative example, the step of applying at least two saturation pulses may comprise applying a first saturation pulse and a second saturation pulse at different times during the cardiac cycle, wherein the first saturation time delay begins from the application of the first saturation pulse, and the second saturation time delay begins from the application of the second saturation pulse. In other words, in FIG. 1b, the method comprises applying the first saturation pulse, waiting a first saturation time delay, and then performing a first image acquisition. Then, the method comprises applying a second saturation pulse, waiting a second saturation time delay, and then performing a second image acquisition. That is, the two sets or blocks of image acquisition shown in FIG. 1b may be performed (each obtaining multiple slices) in each cardiac cycle, each after a different time following a different saturation pulse. In this case, the first saturation time delay may be longer than the second saturation time delay, or vice-versa.

In FIG. 1b, the first image acquisition is shown as being performed after a long saturation time delay (LTS), and the second image acquisition is shown as being performed after a short saturation time delay (STS). It will be understood that this is a non-limiting illustrative example, and each image acquisition may be performed after any saturation time delay length.

The step of performing the first image acquisition may comprise simultaneously obtaining at least two image slices during a first cardiac phase, and the step of performing the second image acquisition may comprise simultaneously obtaining at least two image slices during a second cardiac phase. The first cardiac phase may be during end systole, and the second cardiac phase may be during mid-diastole, but it will be understood that this is a non-limiting example of the cardiac phases during which image slices may be obtained.

The steps of performing a first and second image acquisition may comprise simultaneously obtaining three image slices corresponding to basal, mid, and apical segments of the heart, but it will be understood that this is a non-limiting example of the different segments that may be imaged.

As mentioned above, saturation time delays that are longer than those used in conventional CMR perfusion imaging techniques may be used in the present techniques to improve the signal ratio and contrast-to-noise ratio. Typically, short saturation time delays of around 100 ms may be used in the conventional techniques. Thus, one of the first saturation time delay and second saturation time delay may have a length in the range of 50 ms to 150 ms (i.e. a short time delay), and the other of the first saturation time delay and second saturation time delay may have a length in the range of 200 ms to 400 ms, or between 200 ms to 600 ms (i.e. a long time delay). It will be understood that both the first and second saturation time delays may be short or long time delays, of differing values. Again, these ranges are non-limiting examples and the first and second saturation time delays may be any suitable values.

The step of performing at least two image acquisitions may comprise using two-dimensional imaging.

Thus, the perfusion sequence of the present techniques provides dual phase and dual contrast data using multi-slice imaging at two different saturation delay times, but it is understood that this choice is customizable and indeed, for example, trial phase and trial contrast data should be achievable.

Figure 2B:
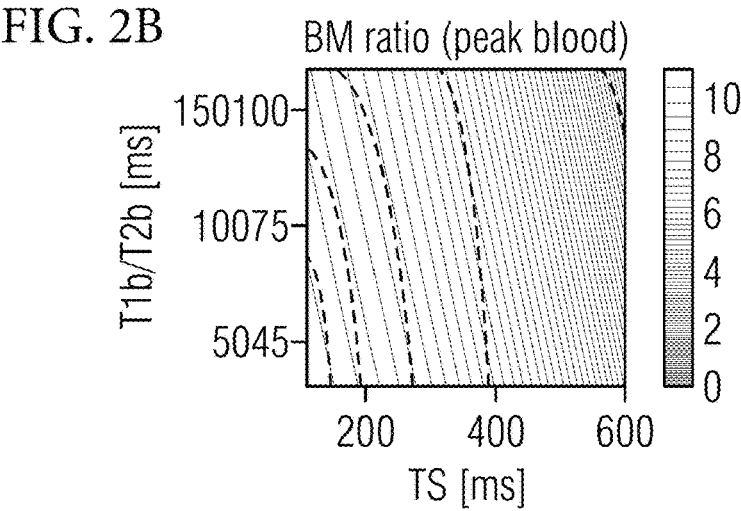
Figure 2C:
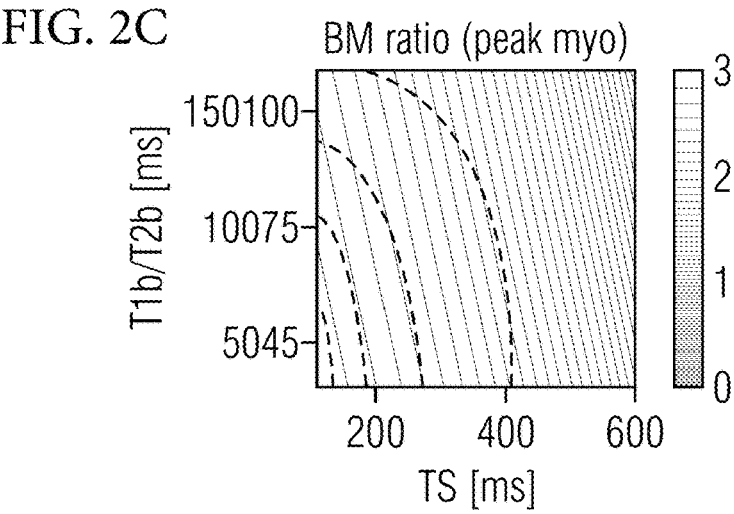

FIGS. 2a-2c show the outcome of numerical simulations used to study the relationship between saturation delay time, contrast between healthy and defective tissue (MD contrast, FIG. 2a), and the blood to myocardium signal ratio (BM ratio, FIGS. 2b and 2c). The impact of saturation delay time (TS) on MD contrast and BM ratio were evaluated using numerical simulations performed using EPG signal formalism. The following sequence parameters were employed: flip angle $\alpha=45°$, TR=2.56 ms, start-up pulses=6, number of bSSFP readout pulses=70. For MD contrast, myocardial T1 (T1m) and T2 (T2m) times were set to 250 ms and 44 ms respectively. A range of simulated myocardial defect T1/T2 times (T1d/T2d) were evaluated from 400/46 ms to 1200/50 ms. For the BM signal ratios, both peak blood (T1m/T2m=1200 ms/50 ms) and peak myocardium (T1m/T2m=250 ms/44 ms) conditions were simulated. Blood T1/T2 (T1b/T2b) simulated range was 28.5/26.5 ms to 168.8/108.7 ms.

FIG. 2a shows MD contrast plotted as a function of TS and defect T1 times (T1d) simulated at peak myocardium. The dashed line highlights the TS/T1d combination with highest MD contrast. The simulations showed that MD contrast is maximized for a TS range of 300-500 ms. FIGS. 2b and 2c show the BM ratio calculated as a function of TS and blood T1/T2 times (T1b/T2b) at simulated peak blood (FIG. 2b) and peak myocardium (FIG. 2c). The simulations show that the BM ratio decreases with increasing TS. In both FIGS. 2a and 2b, the quantities were evaluated at k-space center.

FIGS. 3a and 3b show the outcome of in-vivo evaluation of an example imaging sequence structure, in accordance with the one or more embodiments of the present disclosure. A proposed prototype sequence consists of two image acquisition blocks acquired in each heartbeat with different saturation times, as shown in FIG. 1b. Specifically, the first image acquisition is performed after a saturation time delay of 300 ms ("LTS," FIG. 3b), and the second image acquisition is performed a saturation time delay of 130 ms ("STS," FIG. 3a). Three slices (base, mid, apex) are imaged using SMS-bSSFP with GC-LOLA correction and a multi-band factor of 3. T-GRAPPA acceleration (R=7) and phase oversampling (300%) are employed for an effective in-plane acceleration of 2.3. Images were reconstructed with an inline prototype non-linear iterative reconstruction algorithm with spatial/temporal L1 regularization. Slice separation is achieved along the phase encoding direction where the (shifted) slices are reconstructed on the oversampled field of view.

Three triple-band pulses with CAIPIRINHA radio-frequency phase increments of −120°, 0°, and 120° for slices 1, 2, and 3 were generated as the complex summation of a native single band (SB) pulse. This achieves shifts in image space of −FOV/3, 0, and FOV/3 for slices 1, 2, and 3, which results in lower g-factor amplification at reconstruction. However, because each band is subject to an independent phase cycling scheme, the frequency response of the bSSFP signal is also shifted. For slices 1, 2, and 3, these shifts equal to −⅓, 0, and ⅓ of the native bSSFP passband interval. The GC-LOLA framework addresses this undesirable effect by (i) applying an additional slice unbalancing gradient within each TR interval to align the frequency response of each band, and (ii) adding an additional GC-LOLA phase cycling term to center the frequency response of the (now aligned) bands onto the water peak.

The proposed prototype sequence was evaluated in five patients referred for contrast CMR at 1.5 T using an 18-element body coil and a 32-channel spine coil. All data was acquired using the following parameters: FOV=360×360 mm2, slice thickness=10 mm, resolution=2.3×2.3 mm2, TR=2.56 ms, TE=1.09 ms, flip angle α=45°, readout bandwidth=1008 Hz/Px, start-up pulses=6, number of bSSFP readout pulses=70, readout duration=179 ms, total acquisition time within a heartbeat=608 ms. The slice gap was adjusted for each patient to cover base, mid and apical regions. Each patient underwent late gadolinium enhancement (LGE) imaging (one patient was LGE positive). A contrast dose of 0.075 mmol/kg (4 cases) or 0.150 mmol/kg (1 case) was injected. Patients performed an exhale breath-hold during first pass perfusion.

LTS and STS data were compared as follows: blood pool and left ventricular myocardium were segmented at baseline, peak blood, and peak myocardial enhancement. Contrast between peak and baseline myocardium (used as a surrogate for defect) is reported. BM ratios at peak blood and peak myocardium were calculated.

FIGS. 3a and 3b show acquired data using saturation delay times (TS) of 130 ms (FIG. 3a) and 300 ms (FIG. 3b) on one exemplary subject without perfusion deficit. Top to bottom: the three simultaneously excited slices (base, mid, apex). Left to right: baseline frame, peak blood, and peak myocardium.

The results shown in FIGS. 3a and 3b are in-line with the simulation results shown in FIGS. 2a-2c. Specifically, across all five patients (where a single patient's data is shown in FIGS. 3a-3b), LTS images led to higher peak to baseline myocardium contrast (158±21%, p<0.01), as well as decreased BM ratio at peak blood (62±13%) and peak myocardium (79±12%). In the LGE-positive patient (FIG. 5), myocardial/scar contrast increased by 158% at peak myocardial enhancement.

FIGS. 4a-4c show a difference in contrast using short saturation time delays and long saturation time delays for the in-vivo testing. Dark versus light bars refer to the images acquired at STS and LTS, respectively. FIG. 4a shows the measured peak myocardium to baseline contrast for the five patients. FIGS. 4b and 4c shown BM ratio calculated at peak blood and peak myocardial enhancement, respectively.

Figure 5:
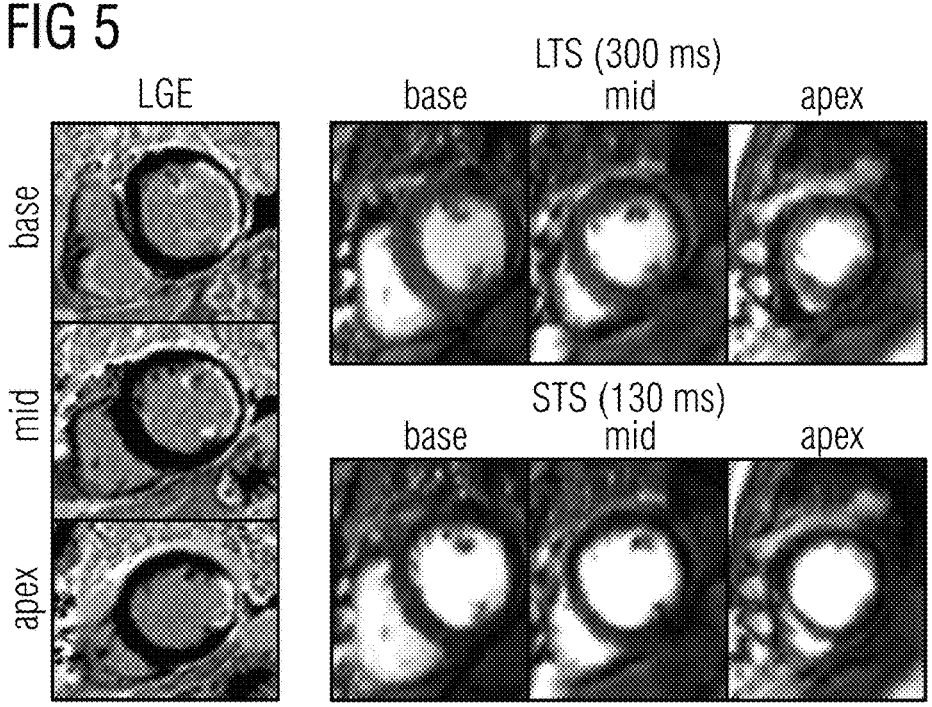
FIG. 5 shows in-vivo data of an LGE-positive patient, in accordance with one or more embodiments of the present disclosure.

FIG. 5 shows in-vivo data of an LGE-positive patient. Specifically, the images on the left show LGE images taken at base, mid, and apex, and the images on the right show dual contrast perfusion data acquired at short (bottom) and long (top) saturation delay times TS.

It is clear from the simulations and in-vivo testing that the proposed perfusion sequence of dual phase imaging with two different saturation delay times enables a 150% increase of myocardial to defect contrast, and a decrease in the blood to myocardium signal ratio by between 60-80% when using a long saturation delay time (LTS), compared to conventional short saturation delay time (STS) images.

Figure 6:
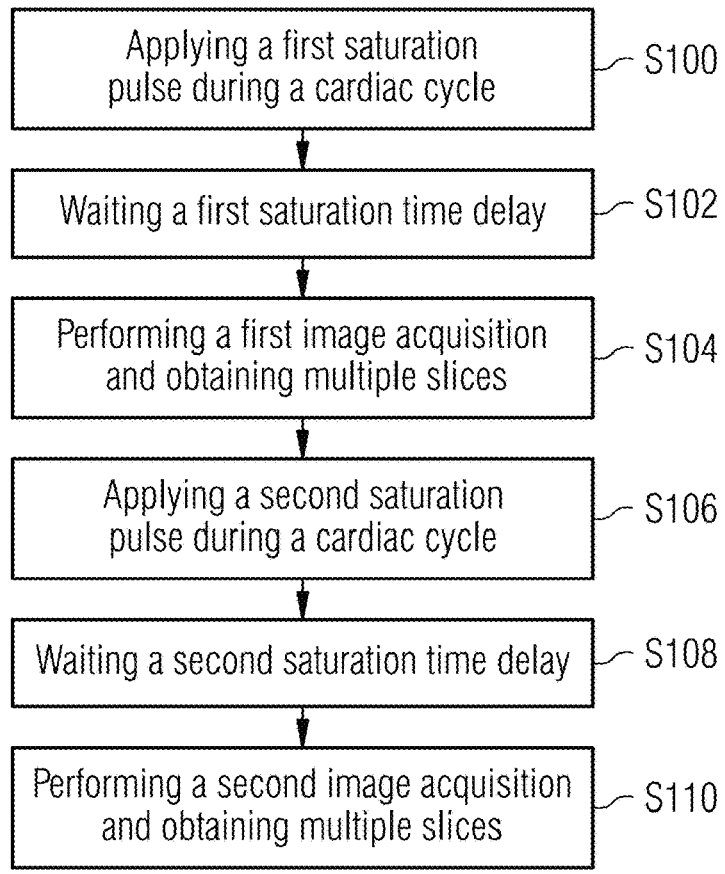
FIG. 6 shows a flow chart showing example steps to obtain images, in accordance with one or more embodiments of the present disclosure.

FIG. 6 shows a flow chart showing example steps to obtain images, in accordance with one or more embodiments of the present disclosure. The method comprises applying at least two saturation pulses during a cardiac cycle or heartbeat. The saturation pulses are applied at different times during the cardiac cycle, i.e. during different cardiac phases. The method then comprises performing at least two image acquisitions, which each take place after a different saturation time delay following the at least two saturation pulses. Each image acquisition comprises simultaneously exciting at least two different slice locations in the heart and simultaneously obtaining at least two image slices.

Thus, the method may comprise applying a first saturation pulse (step S100), waiting a first saturation time delay (step S102), and then performing, after the first saturation time delay, a first image acquisition comprising simultaneously exciting at least two different slice locations in the heart and simultaneously obtaining at least two image slices (step S104). Subsequently, the method may comprise applying a second saturation pulse (step S106), waiting a second saturation time delay (step S108), and then performing, after the second saturation time delay, a second image acquisition comprising simultaneously exciting the at least two different slice locations in a heart and simultaneously obtaining at least two image slices (step S110), wherein the second saturation time delay is of a different length to the first saturation time delay.

The operations described and depicted in the illustrative methods of FIG. 6 may be carried out or performed in any suitable order as desired in various example embodiments of the disclosure. Additionally, in certain example embodiments, at least a portion of the operations may be carried out in parallel. Furthermore, in certain example embodiments, less, more, or different operations than those depicted in FIG. 6 may be performed.

Figure 7:
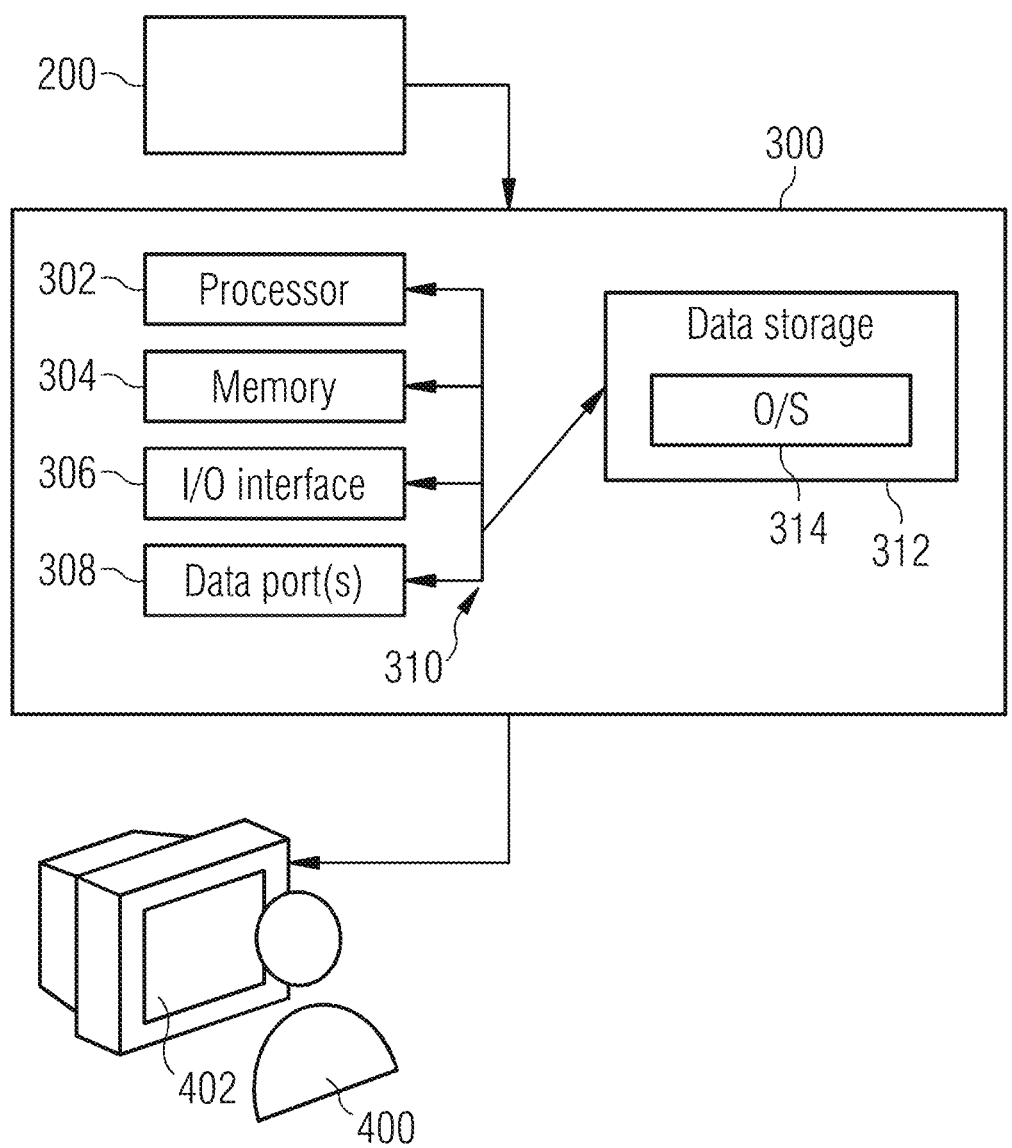
FIG. 7 is a block diagram of a system which may be used to carry out the method(s) described herein, in accordance with one or more embodiments of the present disclosure.

FIG. 7 is a block diagram of a system which may be used to carry out the method(s) described herein, in accordance with one or more embodiments of the present disclosure. The image capture system comprises an image processor 300 that may be used to perform image processing. An imaging system 200, e.g. an X-ray machine, an MRI scanner or the like, captures images that are sent to the image processor 300. The outputs from the image processor 300 may be output to a user 400 via any suitable user interface 402, e.g. a screen on a computer or other electronic device.

The image processor 300 may be formed from one or more local, remote, or cloud servers.

The image processor 300 may include one or more processors 302, one or more memory devices 304 (generically referred to herein as memory 304), one or more input/output ("I/O") interface(s) 306, one or more data ports 308, and data storage 312. The image processor 300 may further include one or more buses 310 that functionally couple various components of the image processor 300.

The data storage 312 may store one or more operating systems (O/S) 314; and one or more program modules, applications, engines, computer-executable code, scripts, or the like. Any of the components depicted as being stored in data storage 312 may include any combination of software, firmware, and/or hardware. The software and/or firmware may include computer-executable code, instructions, or the like that may be loaded into the memory 304 for execution by one or more of the processor(s) 302 to perform any of the operations described earlier in connection with correspondingly named engines and/or methods described herein in accordance with the various embodiments.

The bus(es) 310 may include at least one of a system bus, a memory bus, an address bus, or a message bus, and may permit exchange of information (e.g., data (including computer-executable code), signaling, etc.) between various components of the image processor 300. The bus(es) 310 may include, without limitation, a memory bus or a memory controller, a peripheral bus, an accelerated graphics port, and so forth. The bus(es) 310 may be associated with any suitable bus architecture including, without limitation, an Industry Standard Architecture (ISA), a Micro Channel Architecture (MCA), an Enhanced ISA (EISA), a Video Electronics Standards Association (VESA) architecture, an Accelerated Graphics Port (AGP) architecture, a Peripheral Component Interconnects (PCI) architecture, a PCI-Express architecture, a Personal Computer Memory Card International Association (PCMCIA) architecture, a Universal Serial Bus (USB) architecture, and so forth.

The memory 304 of the image processor 300 may include volatile memory (memory that maintains its state when supplied with power) such as random access memory (RAM) and/or non-volatile memory (memory that maintains its state even when not supplied with power) such as read-only memory (ROM), flash memory, ferroelectric RAM (FRAM), and so forth. Persistent data storage, as that term is used herein, may include non-volatile memory. In certain example embodiments, volatile memory may enable faster read/write access than non-volatile memory. However, in certain other example embodiments, certain types of non-volatile memory (e.g., FRAM) may enable faster read/write access than certain types of volatile memory.

In various implementations, the memory 304 may include multiple different types of memory such as various types of static random access memory (SRAM), various types of dynamic random access memory (DRAM), various types of unalterable ROM, and/or writeable variants of ROM such as electrically erasable programmable read-only memory (EEPROM), flash memory, and so forth. The memory 304 may include main memory as well as various forms of cache memory such as instruction cache(s), data cache(s), translation lookaside buffer(s) (TLBs), and so forth. Further, cache memory such as a data cache may be a multi-level cache organized as a hierarchy of one or more cache levels (L1, L2, etc.).

The data storage 312 may include removable storage and/or non-removable storage including, but not limited to, magnetic storage, optical disk storage, and/or tape storage. The data storage 312 may provide non-volatile storage of computer-executable instructions and other data. The memory 304 and the data storage 312, removable and/or non-removable, are examples of computer-readable storage media (CRSM).

The data storage 312 may store computer-executable code, instructions, or the like that may be loadable into the memory 304 and executable by the processor(s) 302 to cause the processor(s) 302 to perform or initiate various operations. The data storage 312 may additionally store data that may be copied to memory 304 for use by the processor(s) 302 during the execution of the computer-executable instructions. Moreover, output data generated as a result of execution of the computer-executable instructions by the processor(s) 302 may be stored initially in memory 304, and may ultimately be copied to data storage 312 for non-volatile storage.

The data storage 312 may further store various types of data utilized by components of the image processor 300. Any data stored in the data storage 312 may be loaded into the memory 304 for use by the processor(s) 302 in executing computer-executable code. In addition, any data depicted as being stored in the data storage 312 may potentially be stored in one or more of the data stores and may be accessed and loaded in the memory 304 for use by the processor(s) 302 in executing computer-executable code.

The processor(s) 302 may be configured to access the memory 304 and execute computer-executable instructions loaded therein. For example, the processor(s) 302 may be configured to execute computer-executable instructions of the various program modules, applications, engines, or the like of the system to cause or facilitate various operations to be performed in accordance with one or more embodiments of the disclosure. The processor(s) 302 may include any suitable processing unit capable of accepting data as input, processing the input data in accordance with stored computer-executable instructions, and generating output data. The processor(s) 302 may include any type of suitable processing unit including, but not limited to, a central processing unit, a microprocessor, a Reduced Instruction Set Computer (RISC) microprocessor, a Complex Instruction Set Computer (CISC) microprocessor, a microcontroller, an Application Specific Integrated Circuit (ASIC), a Field-Programmable Gate Array (FPGA), a System-on-a-Chip (SoC), a digital signal processor (DSP), and so forth. Further, the processor(s) 302 may have any suitable microarchitecture design that includes any number of constituent components such as, for example, registers, multiplexers, arithmetic logic units, cache controllers for controlling read/write operations to cache memory, branch predictors, or the like. The microarchitecture design of the processor(s) 302 may be capable of supporting any of a variety of instruction sets.

Referring now to other illustrative components depicted as being stored in the data storage 312, the O/S 314 may be loaded from the data storage 312 into the memory 304 and may provide an interface between other application software executing on the image processor 300 and hardware resources of the image processor 300. More specifically, the O/S 314 may include a set of computer-executable instructions for managing hardware resources of the system and for providing common services to other application programs (e.g., managing memory allocation among various application programs). In certain example embodiments, the O/S 314 may control execution of one or more of the program modules depicted as being stored in the data storage 312. The O/S 314 may include any operating system now known or which may be developed in the future including, but not limited to, any server operating system, any mainframe operating system, or any other proprietary or non-proprietary operating system.

Referring now to other illustrative components of the image processor 300, the input/output (I/O) interface(s) 306 may facilitate the receipt of input information by the image processor 300 from one or more I/O devices as well as the output of information from the image processor 300 to the one or more I/O devices. The I/O devices may include any of a variety of components such as a display or display screen having a touch surface or touchscreen; an audio output device for producing sound, such as a speaker; an audio capture device, such as a microphone; an image and/or video capture device, such as a camera; a haptic unit; and so forth. Any of these components may be integrated into the image processor 300 or may be separate. The I/O devices may further include, for example, any number of peripheral devices such as data storage devices, printing devices, and so forth.

The I/O interface(s) 306 may also include an interface for an external peripheral device connection such as universal serial bus (USB), FireWire, Thunderbolt, Ethernet port or other connection protocol that may connect to one or more networks. The I/O interface(s) 306 may also include a connection to one or more antennas to connect to one or more networks via a wireless local area network (WLAN) (such as Wi-Fi) radio, Bluetooth, and/or a wireless network radio, such as a radio capable of communication with a wireless communication network such as a Long Term Evolution (LTE) network, WiMAX network, 3G network, etc.

The image processor 300 may further include one or more data ports 310 via which the image processor 300 may communicate with any of the processing modules. The data ports(s) 310 may enable communication with the image capture device 200 and the database 500.

It should be appreciated that the engines and the program modules depicted in the Figures are merely illustrative and not exhaustive, and that processing described as being supported by any particular engine or module may alternatively be distributed across multiple engines, modules, or the like, or performed by a different engine, module, or the like. In addition, various program module(s), script(s), plug-in(s), Application Programming Interface(s) (API(s)), or any other suitable computer-executable code hosted locally on the system and/or hosted on other computing device(s) accessible via one or more of the network(s), may be provided to support the provided functionality, and/or additional or alternate functionality. Further, functionality may be modularized differently such that processing described as being supported collectively by the collection of engines or the collection of program modules may be performed by a fewer or greater number of engines or program modules, or functionality described as being supported by any particular engine or module may be supported, at least in part, by another engine or program module. In addition, engines or program modules that support the functionality described herein may form part of one or more applications executable across any number of devices of the system in accordance with any suitable computing model such as, for example, a client-server model, a peer-to-peer model, and so forth. In addition, any of the functionality described as being supported by any of the engines or program modules may be implemented, at least partially, in hardware and/or firmware across any number of devices.

It should further be appreciated that the system may include alternate and/or additional hardware, software, or firmware components beyond those described or depicted without departing from the scope of the disclosure. More particularly, it should be appreciated that software, firmware, or hardware components depicted as forming part of the system are merely illustrative and that some components may not be present or additional components may be provided in various embodiments. While various illustrative engines have been depicted and described as software engines or program modules, it should be appreciated that functionality described as being supported by the engines or modules may be enabled by any combination of hardware, software, and/or firmware. It should further be appreciated that each of the above-mentioned engines or modules may, in various embodiments, represent a logical partitioning of supported functionality. This logical partitioning is depicted for ease of explanation of the functionality and may not be representative of the structure of software, hardware, and/or firmware for implementing the functionality. Accordingly, it should be appreciated that functionality described as being provided by a particular engine or module may, in various embodiments, be provided at least in part by one or more other engines or modules. Further, one or more depicted engines or modules may not be present in certain embodiments, while in other embodiments, additional engines or modules not depicted may be present and may support at least a portion of the described functionality and/or additional functionality. Moreover, while certain engines modules may be depicted or described as sub-engines or sub-modules of another engine or module, in certain embodiments, such engines or modules may be provided as independent engines or modules or as sub-engines or sub-modules of other engines or modules.

Although specific embodiments of the disclosure have been described, one of ordinary skill in the art will recognize that numerous other modifications and alternative embodiments are within the scope of the disclosure. For example, any of the functionality and/or processing capabilities described with respect to a particular system, system component, device, or device component may be performed by any other system, device, or component. Further, while various illustrative implementations and architectures have been described in accordance with embodiments of the disclosure, one of ordinary skill in the art will appreciate that numerous other modifications to the illustrative implementations and architectures described herein are also within the scope of this disclosure.

Certain aspects of the disclosure are described above with reference to block and flow diagrams of systems, methods, apparatuses, and/or computer program products according to example embodiments. It will be understood that one or more blocks of the block diagrams and flow diagrams, and combinations of blocks in the block diagrams and the flow diagrams, respectively, may be implemented by execution of computer-executable program instructions. Likewise, some blocks of the block diagrams and flow diagrams may not necessarily need to be performed in the order presented, or may not necessarily need to be performed at all, according to some embodiments. Further, additional components and/or operations beyond those depicted in blocks of the block and/or flow diagrams may be present in certain embodiments.

Accordingly, blocks of the block diagrams and flow diagrams support combinations of means for performing the specified functions, combinations of elements or steps for performing the specified functions, and program instruction means for performing the specified functions. It will also be understood that each block of the block diagrams and flow diagrams, and combinations of blocks in the block diagrams and flow diagrams, may be implemented by special-purpose, hardware-based computer systems that perform the specified functions, elements or steps, or combinations of special-purpose hardware and computer instructions.

Program modules, applications, or the like disclosed herein may include one or more software components including, for example, software objects, methods, data structures, or the like. Each such software component may include computer-executable instructions that, responsive to execution, cause at least a portion of the functionality described herein (e.g., one or more operations of the illustrative methods described herein) to be performed.

A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform.

Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, or a report writing language. In one or more example embodiments, a software component comprising instructions in one of the foregoing examples of programming languages may be executed directly by an operating system or other software component without having to be first transformed into another form.

A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

Software components may invoke or be invoked by other software components through any of a wide variety of mechanisms. Invoked or invoking software components may comprise other custom-developed application software, operating system functionality (e.g., device drivers, data storage (e.g., file management) routines, other common routines and services, etc.), or third-party software components (e.g., middleware, encryption, or other security software, database management software, file transfer or other network communication software, mathematical or statistical software, image processing software, and format translation software).

Software components associated with a particular solution or system may reside and be executed on a single platform or may be distributed across multiple platforms. The multiple platforms may be associated with more than one hardware vendor, underlying chip technology, or operating system. Furthermore, software components associated with a particular solution or system may be initially written in one or more programming languages, but may invoke software components written in another programming language.

Computer-executable program instructions may be loaded onto a special-purpose computer or other particular machine, a processor, or other programmable data processing apparatus to produce a particular machine, such that execution of the instructions on the computer, processor, or other programmable data processing apparatus causes one or more functions or operations specified in the flow diagrams to be performed. These computer program instructions may also be stored in a computer-readable storage medium (CRSM) that upon execution may direct a computer or other programmable data processing apparatus to function in a particular manner, such that the instructions stored in the computer-readable storage medium produce an article of manufacture including instruction means that implement one or more functions or operations specified in the flow diagrams. The computer program instructions may also be loaded onto a computer or other programmable data processing apparatus to cause a series of operational elements or steps to be performed on the computer or other programmable apparatus to produce a computer-implemented process.

Additional types of CRSM that may be present in any of the devices described herein may include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile disc (DVD) or other optical storage, magnetic cassettes, magnetic tape, magnetic disk storage or other magnetic storage devices, or any other medium which can be used to store the information and which can be accessed. Combinations of any of the above are also included within the scope of CRSM. Alternatively, computer-readable communication media (CRCM) may include computer-readable instructions, program modules, or other data transmitted within a data signal, such as a carrier wave, or other transmission. However, as used herein, CRSM does not include CRCM.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

What is claimed is:

1. A method, comprising:
    performing cardiac magnetic resonance (CMR) perfusion imaging by:
        applying two saturation pulses during a cardiac cycle; and
        performing two image acquisitions, each of the two image acquisitions occurring after (i) one of the at least two saturation pulses, and (ii) a different saturation time delay,
    wherein performing the two image acquisitions comprises, for each one of the two image acquisitions, (i) simultaneously exciting a set of different slice locations in the heart, and (ii) simultaneously obtaining a set of image slices corresponding to the set of different slice locations.

2. The method as claimed in claim 1, wherein applying the two saturation pulses comprises applying a first saturation pulse and a second saturation pulse at different times during the cardiac cycle, and
    wherein performing the two image acquisitions comprises:
        performing, after a first saturation time delay after application of the first saturation pulse, a first image acquisition comprising simultaneously exciting the set of different slice locations in the heart and simultaneously obtaining the set of image slices;
        performing, after a second saturation time delay after application of the second saturation pulse, a second image acquisition comprising simultaneously exciting the set of different slice locations in the heart and simultaneously obtaining the set of image slices,
    wherein the second saturation time delay is of a different length than the first saturation time delay.

3. The method as claimed in claim 2, wherein the first saturation time delay is shorter than the second saturation time delay.

4. The method as claimed in claim 2, wherein the first saturation time delay is longer than the second saturation time delay.

5. The method as claimed in claim 2, wherein one of the first saturation time delay and the second saturation time delay has a value in a range of 50 ms to 150 ms, and
   wherein the other of the first saturation time delay and second saturation time delay has a value in a range of 200 ms to 600 ms.

6. The method as claimed in claim 1, wherein performing the two image acquisitions comprises using at least one of two-dimensional imaging, simultaneous multi-slice (SMS) imaging, or three-dimensional imaging.

7. The method as claimed in claim 1, wherein performing the two image acquisitions comprises:
   performing a first image acquisition comprising simultaneously obtaining the set of image slices during a first cardiac phase; and
   performing a second image acquisition comprising simultaneously obtaining the set of image slices during a second cardiac phase.

8. The method as claimed in claim 7, wherein the first cardiac phase is an end-systole cardiac phase, and
   wherein the second cardiac phase is a mid-diastole cardiac phase.

9. The method as claimed in claim 1, wherein performing the two image acquisitions comprises:
   performing a first and second image acquisition by simultaneously obtaining three image slices during the first and second image acquisition, respectively, corresponding to basal, mid, and apical segments of the heart.

10. The method as claimed in claim 1, wherein performing the two image acquisitions comprises:
    using at least one of balanced steady state free precession, gradient echo, and echoplanar imaging as a magnetic resonance imaging (MRI) readout module.

11. The method as claimed in claim 1, wherein the act of performing the two image acquisitions comprises:
    for each one of the two image acquisitions, (i) simultaneously exciting, as the set of different slice locations, three different slice locations in the heart, and (ii) simultaneously obtaining, as the set of different image slices, three image slices corresponding to the three different slice locations in the heart.

12. A non-transitory computer-readable medium having processor control code stored thereon that, when executed by a system, causes the system to:
    perform cardiac magnetic resonance (CMR) perfusion imaging of a heart by:
        applying two saturation pulses during a cardiac cycle; and
        performing two image acquisitions, each of the two image acquisitions occurring after (i) one of the at least two saturation pulses, and (ii) a different saturation time delay,
        wherein performing the two image acquisitions comprise, for each one of the two image acquisitions, (i) simultaneously exciting a set of different slice locations in the heart, and (ii) simultaneously obtaining a set of image slices corresponding to the set of different slice locations.

13. An image capture system, comprising:
    an imager configured to capture images for performing cardiac magnetic resonance (CMR) perfusion imaging by:
        applying two saturation pulses during a cardiac cycle; and
        performing two image acquisitions, each of the two image acquisitions occurring after (i) one of the at least two saturation pulses, and (ii) a different saturation time delay, the two image acquisitions being performed by, for each one of the two image acquisitions, (i) simultaneously exciting a set of different slice locations in the heart, and (ii) simultaneously obtaining a set of image slices corresponding to the set of different slice locations; and
    a display configured to present the set of image slices captured by the image capture device.

* * * * *